United States Patent [19]

Curtis

[11] Patent Number: 4,476,858
[45] Date of Patent: Oct. 16, 1984

[54] SHOE-FOOT INTERFACE

[76] Inventor: R. Stephen Curtis, 2828 Lemmon Ave., Dallas, Tex. 75204

[21] Appl. No.: 453,469

[22] Filed: Dec. 27, 1982

[51] Int. Cl.³ .............................................. A61F 13/00
[52] U.S. Cl. ..................................... 128/80 R; 128/165
[58] Field of Search .................. 128/166, 166.5, 80 R, 128/80 H, 156, 167, 165; 2/239, 240, 241

[56] References Cited

U.S. PATENT DOCUMENTS

| | | |
|---|---|---|
| 822,138 | 5/1906 | Little . |
| 991,831 | 5/1911 | Collis . |
| 1,040,279 | 10/1912 | Collis . |
| 1,084,197 | 1/1914 | Collis . |
| 1,220,724 | 3/1917 | Burns . |
| 1,365,512 | 1/1921 | Lewis ................................ 128/166.5 |
| 1,406,583 | 2/1922 | Ruge .................................. 128/166.5 |
| 1,443,844 | 1/1923 | Jensen . |
| 1,462,534 | 7/1923 | Condylis et al. . |
| 1,478,253 | 12/1923 | Quenzer . |
| 1,565,259 | 12/1925 | Collis . |
| 2,010,749 | 8/1935 | Cartledge . |
| 3,266,058 | 5/1964 | Guttman . |
| 4,085,745 | 4/1978 | Alenares ............................. 128/165 |

Primary Examiner—John D. Yasko
Attorney, Agent, or Firm—Jerry W. Mills; Gregory M. Howison; Nina Medlock

[57] ABSTRACT

An orthotic shoe-foot interface includes a shock absorbing layer that is selectively disposed over the bony prominences of the foot and the tendon attachment areas of selected ones of tendons of the foot. An area of shock absorbing material (12) covers the calcaneal prominence, an area of shock absorbing material (14) covers the heads of the matatarsal bones and an area of shock absorbing material (16) covers the base of the fifth metatarsal bone. Areas of shock absorbing material (22) and (30) cover the posterior and anterior tibial tendon attachment points to cause compression thereof. The Achilles tendon is covered by an area of shock absorbing material (20) that also covers the attachment point of the Achilles tendon into the calcaneal bone. The tendons attached to the great toe on the medial side thereof are covered by an area of shock absorbing material (24) and the tendons attaching to the small toe on the lateral side thereof are covered by an area of shock absorbing material (26). Tendons attached to the base of the fifth metatarsal are covered by an area of shock absorbing material (28). An elastic layer is attached to the shock absorbing layer to form an overall sock exclusive of the toes that, when disposed between the shoe and the foot, provides both a shock-absorbing function and a shoe-filling function to reduce the amount of the shock imparted to the bony prominences of the foot and the tendon attachments thereto in addition to preventing foot slippage within the shoe.

18 Claims, 6 Drawing Figures

SHOE-FOOT INTERFACE

TECHNICAL FIELD

This invention relates in general to anatomical padding devices and, more particularly, to footwear worn by active people, especially support footwear worn by athletes.

BACKGROUND OF THE INVENTION

In the past, athletes have been provided with very basic footwear in the form of a very thin canvas topped and flat soled tennis shoe. When physical problems ensued from the strenous exercise that was normally undertaken by the athlete, the normal remedy was to insert an orthotic inside the shoe as needed. Present day shoes, currently manufactured by many companies, have progressed far from this early shoe and often neither an over-the-counter nor a "specially" made orthotic is needed. The shoes themselves function as an orthotic. This has resulted in far less foot problems for the general public.

In general, manufactured shoes are constructed for people with relatively symmetrical, evenly sized feet. For these people, the shoes can function to carry them many relatively pain-free miles with few problems. For those that do not fit into this category, however, the structured stability that has improved the shoes also results in a semirigidity that makes these shoes semiunforgiving to an active foot. This is particularly so in the "aging" foot, especially over their bony prominences and tendon insertions.

In the athlete's case, many of their lower extremity problems involve overuse and training errors such as rapidly accelerating distances or speeds. However, some of the injuries are due solely to the shoes they are wearing. For example, if an athlete wears shoes long enough to protect his toes, a possibility exists that his foot slips up and down in the mid and hind foot area of the shoe. If the athlete thickens his foot with two socks or fills his shoes with a sole-elevating orthotic, he may overfill his entire shoe including the toe box and, despite the filling, still have a foot that slips. The choices he is left with are to either overtighten his laces, thereby causing the possibility of ankle soreness, or dispose of the shoes and start over. If he chooses to continue wearing his shoes, eventually he will develop a sore arch, heel, forefoot and/or toe and either stop running or continue to run in pain. This problem is as old as the orthotic-prosthetic concept itself.

Prior devices have been proposed for ankle support and to provide protection for the non-ambulatory patient's feet and the like, as exemplified in U.S. Pat. Nos. 822,138, 1,565,259 and 3,226,058. However, these devices do not provide cushioning protection to the sensitive portions of an active foot, and especially, an athletic foot.

In view of the above disadvantages with many of the present day shoes, there exists a need for a form fitted apparatus to better interface the shoe and the foot, to not only cushion the sensitive portions of the active foot by absorbing shock and reducing friction, but also allow the shoe to perform its intended function by virtue of its better overall fit.

SUMMARY OF THE INVENTION

The present invention disclosed and claimed herein comprises a shoe-foot interface that includes a body having cushioned areas that selectively cover bony prominences of the foot and the insertion points of selected ones of the tendons of the foot. The body of the interface allows the toes to move freely when a closed toed shoe such as an athletic shoe is worn over the shoe-foot interface.

The bony prominences covered by the selectively cushioned areas are the calcaneal prominence, the navicular bone, the heads of the metarsal bones and the base of the fifth metatarsal bone. The tendon attachments covered by the selectively cushioned areas include the anterior and posterior tibial attachments about the navicular bone, the common toe extensor tendons over the ankle and the Achilles tendon and its attachment to the calcaneal bone. The attachment points for the abductor tendons of the great toe and the fifth toe are covered by the selective cushioned areas and also the attachment point for the peroneus brevus tendon. The plantar fascia is also covered where it attaches to the anterior ventral portion of the calcaneal bone.

In another embodiment of the present invention, the portions of the cushioned areas that cover the calcaneal bone, the heads of the metatarsal bones and the arch of the foot are comprised of a material having a higher shock-absorbing capability than the cushioned areas covering the remainder of the bony prominences and tendon attachment areas. This provides an additional shock absorbing and dispersing function for these areas.

BRIEF DESCRIPTION OF THE DRAWINGS

For a more complete understanding of the present invention and the advantages thereof, reference is now made to the following description taken in conjunction with the accompanying Drawings in which.

DETAIL DESCRIPTION OF THE INVENTION

Figure 1:
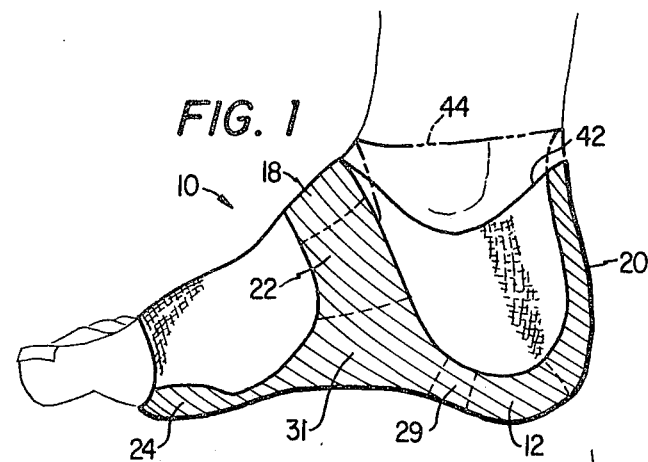
FIG. 1 illustrates a medial view of a foot wearing the shoe-foot interface of the present invention.
Figure 2:
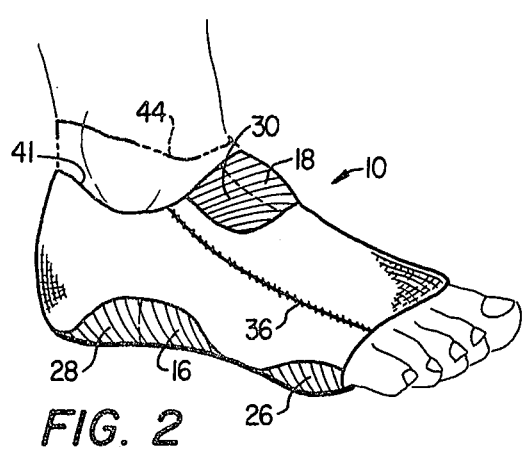
FIG. 2 illustrates the lateral view of the foot in FIG. 1.

FIGS. 1-4 illustrate various views of an athlete's foot with a shoe-foot interface 10 disposed thereon. The shoe-foot interface 10 of the exemplary embodiment is fabricated with two thicknesses of material. The crosshatched area is slightly thicker than the solid area such that the crosshatched area provides selective padding about the anatomy of the foot, as will be described hereinbelow. The interface 10 does not encompass the toes on the foot but, rather, is recessed therefrom to the heads of the metatarsal bones.

The shoe-foot interface 10 is operable to be worn in conjunction with any shoe but, especially, an athletic shoe. The padded area affords selective padding for the bony protuberances and tendon attachment areas, as will be described hereinbelow. By selective padding of these anatomical areas of the foot, the wearer experiences a higher level of comfort due to the fact that pressure exerted upon the foot through forces such as walking, running or jumping is more evenly spread out rather than concentrated at specific areas. By spreading out the forces, the interface 10 partially absorbs the shock of impact of foot strike and, by virtue of the tighter bond created by the interface between the foot and shoe, the force of impact is dispersed more efficiently throughout the foot in a hydraulic manner. This selective padding also prevents slippage of the foot within the shoe itself and potentially reduces tensile forces on tendon insertions by direct compression of the tendon and its attachment to the bone. Further, if desired, the interface device can be cooled to a lower temperature which will reduce inflammation at the bursae that are normally associated with the bony prominences and tendon insertions by taking advantage of the antiinflammatory effect of cold.

Referring now to FIGS. 1-4 and to FIG. 5, which illustrates an exploded view of the shoe-foot interface 10 from an undersole view, the function of the shoe-foot interface will be described. As described above, the shoe-foot interface 10 is fabricated of two thicknesses of material which, for reference, will be referred to as an elastic material and a shock absorbing material. The shock absorbing material (hereinafter referred to as "shock absorbing") is much thicker than the elastic material to provide the absorbing effect. The elastic material covers the areas of the foot not covered by the absorbing materials and provides a supportive function rather than the shock absorbing function of the absorbing material. The interface 10 can be fabricated of a material such as neoprene. However, it should be understood that any material that affords a certain degree of elasticity and padding will suffice.

For simplicty reasons, a plurality of points will be depicted with reference numerals that refer in general to the anatomy of the foot. It should be understood that the referenced areas refer to generalized portions of the anatomy of the foot since slight variations occur between individuals. The areas that the absorbing portions of the interface 10 covers can be divided into two groups, the first group for covering the bony prominences and a second group for covering the tendon insertions. A description of the bony prominences that are covered will be undertaken first. An area of the absorbing material covers the calcaneum, or os calcis, which is the largest and strongest of the tarsal bones. It is irregularly cuboidal in form, having its long axis directed forward and outward. It is situated at the lower and back part of the foot, serving to transmit the weight of the body to the ground, and forming a strong lever for the muscles of the calf. The area 12 is centered primarily around the calcineal prominence, that is, the portion thereof projecting downward and slightly rearward of the foot.

A section 14 of shock absorbing material is disposed adjacent the lowermost distal ends or heads of the five metatarsal bones. With particular reference to the first metatarsal bone, the section 14 covers sesamoid bones that underly the head of the first metatarsal bone. The sesamoid bones are small rounded masses which are developed in those tendons which exert a great amount of pressure upon the parts over which they glide. The proximal end or the base of the fifth metatarsal bone is covered by an area 16 of the absorbing material on the lateral side of the foot. The head of the fifth metatarsal has a tuberosity extending laterally and downward therefrom such that this bony prominence absorbs a large amount of lateral force upon the foot.

A section 18 of shock absorbing material is disposed adjacent the navicular bone which is subjected to a great deal of the medial force which the foot is subjected to under exercise. The areas 12-18 comprise the portions of the absorbing material that is disposed adjacent the bony prominesces to provide padding thereon.

In addition to the bony prominences described above, the remaining portion of the anatomy of the foot that the shock absorbing material covers is the tendon insertions or the points at which the tendons are attached into the bone. A section 20 of shock absorbing material is disposed adjacent the Achilles (tendo calcaneus) tendon and is adjacent the section 12 running vertically up the heel of the foot. The Achilles tendon is the thickest and strongest tendon in the body and is about six inches in length commencing about the middle of the leg. This tendon is inserted into the lower part of the posterior surface of the calcaneal bone and a synovial bursa is interposed between the tendons and the upper part of this surface. Synovial bursa in eneral are found interposed between muscles or tendons as they play over projecting bony surfaces. They consist of a thin wall of connective tissue, partially covered by patches of cells, and contain a viscid fluid. These bursa reduce friction due to the gliding of a tendon over the bony surface.

A section 22 of shock absorbing material is disposed adjacent the portion of the foot proximate to the posterior tibial tendon. The posterior tibial tendon passes through a groove behind the inner maleolis and then passes into the foot and is inserted into the tuberosity of the navicular and internal cuneiform bones. The posterial tibial tendon is a direct extensor of the foot at the ankle joint. Acting in conjunction with the anterior tibial tendon, it is operative to turn the sole of the foot inward (invert the foot). This tendon is an important factor in maintaining the arch of the foot. Therefore, the section 22 provides padding and pressure therefrom directly adjacent the insertion of the posterior tibial tendon into the navicular bone.

A section 24 of shock absorbing material is disposed adjacent the point at which the abductor hallucis inserts into the great toe. The abductor hallucis muscle lies along the inner border of the foot and terminates in a tendon which is inserted into the inner side of the base of the first phalanx of the great toe. A section 26 of the shock absorbing material is disposed adjacent the abductor digiti minimi which is a tendon that arises from a muscle that lies along the outer border of the foot. The tendon, after gliding over a smooth facet on the under surface of the base of the fifth metatarsal bone, is inserted into the outer side of the base of the first phalanx of this toe.

A section 28 of the shock absorbing material is disposed adjacent the insertion point of the tendon that terminates the peroneous brevis muscle. This tendon runs behind the external malleolus and then passes on the outer side of the calcaneal bone. The tendon is inserted into the tuberosity at the base of the fifth metatarsal bone on its outer or lateral side. The peroneous brevis and the peroneous longus muscles are operable to extend the foot upon the leg. The peronei serve to steady the leg upon the foot. This is especially the case in standing upon one leg, when the tendency of the superincumbent weight is to throw the leg inward. These muscles maintain the perpendicular direction of the limb.

A section 30 of shock absorbing material is disposed adjacent the insertion point of the interior tibial tendon into the navicular bone. The Anterior tibial tendon passes over the dorsal side of the navicular bone adjacent the navicular tuberosity and is inserted into the inner and under surface of the internal cuneiform bone and base of the first metatarsal bone. As described above, the Anterior tibial tendon operates in conjunction with the posterior tibial tendon to turn the sole of the foot inward. Therefore, the sections 18, 22, and 30 function to pad the bony prominence of the navicular tuberosity and the tendons which insert on either side thereof. It should be understood that although only the description of the posterior and anterior tibial tendon is discussed, there are a plurality of tendons that pass through sheaths on either side of the navicular tuberosity such as the great toe extensor tendons.

A section 29 of shock absorbing material is disposed between adjacent the section 12 to cover the insertion point of the plantar fascia. The plantar fascia inserts into the inner tuberosity of the calcaneal bone. A section 31 of shock absorbing material is disposed adjacent and between the sections 14, 16, 22, 28, and 29 to cover the remaining portion of the sole of the foot.

Figure 3:
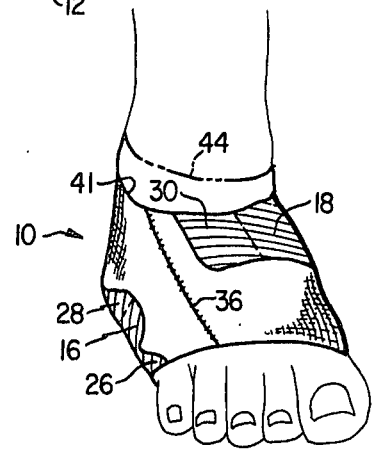
FIG. 3 illustrates a frontal view of the foot wearing the shoe-foot interface.
Figure 4:
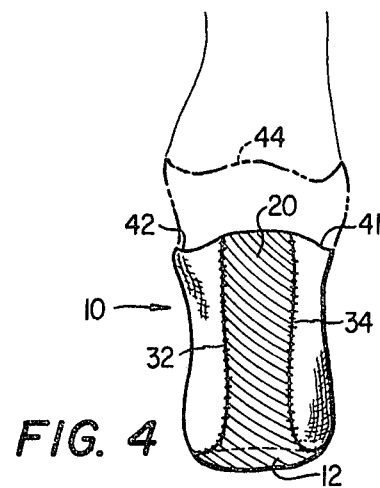
FIG. 4 illustrates a heel view of the foot wearing the shoe-foot interface.

The section 20 of shock absorbing material is attached to the layers of elastic material with seams 32 and 34 attached laterally to the section 20 on either side thereof, as best depicted in FIG. 4. The dorsal portion of the interface 10 is attached by a seam 36 along edges 35 and 37 of the elastic material. The interface 10 is designed to be worn as a pullover sock over the regular sock. The elastic material is of a stretchable type, as described above, to facilitate placement of the interface 10 on the foot prior to putting a shoe on. As shown in FIGS. 1–4, the front portion of the interface 10 extends only to the proximate area of the heads of metatarsal bones. This allows the toes to be free from constriction in the shoe. Since the interface 10 itself provides the shoe filling effect that is necessary to prevent slippage, there is no need for the interface 10 to extend over the toes to prevent any forward motion thereof.

A section of elastic material 38 is disposed adjacent the sections 18, 22, 24 and 30 of shock absorbing material. A section 39 of elastic material is disposed adjacent the sections 12, 18, 22 and 31 of the shock absorbing material. A section 40 of elastic material is disposed adjacent the sections 12, 16, 26 and 28 of the shock absorbing material. The sections of elastic material which are thinner than the shock absorbing material as described above, connect the selectively placed sections of shock absorbing material and are fabricated of a very lightly elasticized material. The sections of elastic material support, to some degree, the arch, forefoot and ankle without adding excessive shoe bulk of exerting excessive pressure that may cause restriction in venus flow pressure.

In the exemplary embodiment shown in FIGS. 1–4, the upper portion of the elastic material along edges 41 and 42 are extended upward and terminate below the malleolus or ankle on either side of the foot. In an alternate embodiment, the edges 41 and 42 extend over the ankle to provide additional support about the ankle, as indicated by the dotted line 44.

Figure 6:
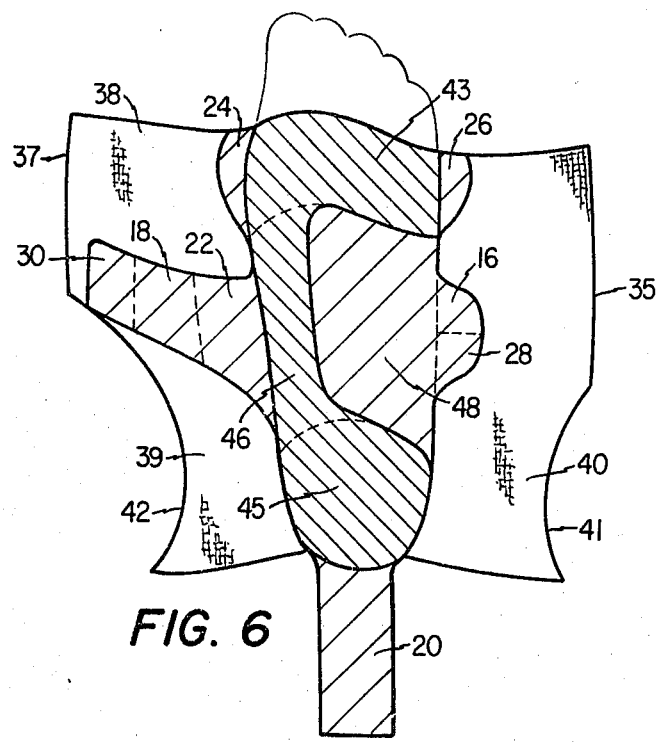
FIG. 6 illustrates an alternate embodiment of the view of the FIG. 5.
Figure 5:
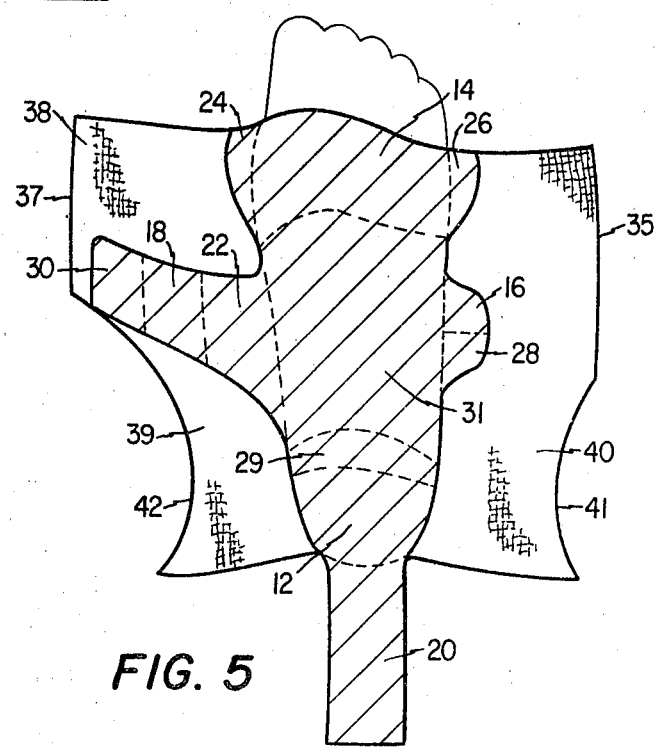
FIG. 5 illustrates an exploded view of the shoe-foot interface taken from the undersole side.

Referring now to FIG. 6, there is illustrated an alternate embodiment of the invention as shown in FIG. 5, wherein like numerals refer to like parts in the various figures. The shoe-foot interface illustrated in FIG. 6 is identical to the shoe-foot interface illustrated in FIG. 5 with the exception of the interface having an increased thickness over the shock absorbing material. This area will be referred to as a thickened area. It should be understood that the material utilized in this thickened area is similar to the shock absorbing material and results in additional shock absorption in the areas covered thereby. The thickened area has an area 43 disposed adjacent the heads of the metatarsal bones that is similar in shape and coverage to the area 14 in FIG. 5. A section 45 on the thickened area is disposed adjacent to the calcaneal prominence and is similar in shape and coverage to the sections 12 and 29 of FIG. 5. Sections 43 and 45 are connected together by an area 46 that is disposed under the arch to provide padding therefore. The remaining portion of the undersole area of the interface in FIG. 3 is covered by a section 48 of shock absorbing material having the areas 16 and 28 protruding therefrom.

In summary, there has been provided an shoe-foot interface that utilizes its selective padding at the bony prominences of the foot and the points of tendon attachment to provide shock absorption for the foot. This padding is worn on the foot and insertable along with the foot into a shoe to provide both a shock absorption during exercise and more fully fill the shoe to prevent slippage of the foot within the shoe. The padding covers the calcaneal prominence and the heads of the metatarsal bones in the lower portion of the foot and the navicular bone with the tendons attached thereabout. In addition, the padding covers the Achilles tendon and the attachment point thereof. A thinner elasticized material is utilized to fill in the portions of the sock to form a complete foot covering with the exception of the toes which are allowed to move freely.

Although the preferred embodiment has been described in detail, it should be understood that various changes, substitutions, and alterations can be made therein without departing from the spirit and scope of the invention as defined by the appended claims.

What I claim is:

1. An orthotic shoe-foot interface for wearing on the foot while wearing a shoe comprising:

a body having shock absorbing areas that selectively cover both the bony prominences of the foot and the insertion points of selected tendons on the foot, said body allowing the toes to move freely when the shoe is worn over the interface while providing a shoe-filling function to enhance the comfort of the shoe while cushioning the wearer's foot; and a second thicker shock absorbing area selectively disposed to cover the anatomical area adjacent the calcaneal prominence, the insertion point of the plantar fascia tendon, the heads of the metatarsal bones and the arch of the foot.

2. The shoe-foot interface of claim 1 wherein at least one of said shock absorbing areas covering the anatomical area adjacent the navicular tuberosity and tendons that are adjacent the navicular tuberosity.

3. The shoe-foot interface of claim 1 wherein at least one of said shock absorbing areas covers the anatomical area adjacent and ventral to the heads of the metatarsal bones.

4. The shoe-foot interface of claim 1 wherein at least one of said shock absorbing areas covers the anatomical area adjacent and ventral to the calcaneal prominence and the insertion point of the plantar fascia tendon.

5. The shoe-foot interface of claim 1 wherein at least one of said shock absorbing areas covers the anatomical area adjacent the base of the fifth metatarsal bone on the lateral tuberosity thereof.

6. The shoe-foot interface of claim 1 wherein at least one of said shock absorbing areas covers the anatomical area adjacent the Achilles tendon and the area adjacent the insertion point of the Achilles tendon into the calcaneus bone.

7. The shoe-foot interface of claim 1 wherein at least one of said shock absorbing areas covers the anatomical area adjacent the insertion point of the abductor hallucis tendon into the great toe.

8. The shoe-foot interface of claim 1 wherein at least one of said shock absorbing areas covers the anatomical area adjacent the peroneus brevus tendon insertion point at the base of the fifth metatarsal bone.

9. The shoe-foot interface of claim 1 wherein at least one of said shock absorbing areas covers the anatomical area adjacent the arch of the foot.

10. The shoe-foot interface of claim 1 further comprising:
a first seam disposed dorsal and lateral to the foot; and
a second and third seam disposed on either side of the Achilles tendon and running parallel therewith.

11. An orthotic shoe-foot interface, comprising:
a body that circumferentially covers the foot of a wearer extending around the metatarsal portion to cover the arch of the foot and extending over the sole and heel of the foot and proximate the ankle without covering the toes;
said body fabricated of an elastic layer and a shock absorbing layer, said shock absorbing layer selectively covering the bony prominences of the foot and the insertion points of selected ones of the tendons of the foot to thereby absorb shock to the foot and fill the shoe; and
the bony prominences covered by said shock absorbing layer comprising the ventral portion of the calcaneal bone, the navicular tuberosity, the dorsal portion of the heads of the metatarsal bones and the tuberosity on the lateral side of the base of the fifth metatarsal bone.

12. The shoe-foot interface of claim 11 wherein the selected ones of the tendons of the foot covered by said shock absorbing layer comprise the Achilles tendon and the insertion thereof into the calcaneal bone, the tendons disposed proximal to the navicular bone, the tendons attached to the medial side of the first metatarsal bone proximate the head thereof, the tendons adjacent to the fifth metatarsal bone proximate to the head thereof, the tendons proximate to the base of the fifth metatarsal bone and the tendons attached to the dorsal interior portion of the calcaneal bone.

13. The shoe-foot interface of claim 11 further comprising:

a first seam disposed dorsal and lateral to the foot; and
a second and third seam disposed on either side of the Achilles tendon and parallel therewith.

14. The shoe-foot interface of claim 11 wherein said shock absorbing layer is comprised of a first shock absorbing layer and a second shock absorbing layer, said second shock absorbing layer thicker than said first shock absorbing layer to provide additional shock absorbance, said second shock absorbing layer disposed adjacent the calcaneal bone and the heads of the metatarsal bones and along the arch of the foot.

15. A shoe-foot interface comprising:
a cushioned layer for absorbing and dispersing shock, said cushioned layer covering the sole of the foot up to and exclusive of the toes and having:
a navicular protrusion for extending over the navicular bone and the tendons proximate thereto,
an Achilles tendon protrusion for extending over the Achilles tendon and its attachment point on the heel of the foot and extending upward along the Achilles tendon to the ankle,
a great toe protrusion for extending over the medial side of the head of the first metatarsal bone and tendon attachments proximate thereto, and
a small toe protrustion for extending over the lateral side of the head of the fifth metatarsal bone and tendon attachments proximate thereto, and
a lateral flap for covering the lateral side of the base of the fifth metatarsal bone and the tendon attachments proximate thereto;
a layer of elastic material attached to said cushioned layer, the combination of said elastic and cushioned layers forming a sock to cover the foot exclusive of the toes and extending around the heel and proximate the ankle.
a lateral seam disposed said layer of elastic material between the dorsal and lateral portions of the foot and extending between the ankle and the border nearest most the toes; and
a first and second heel seam disposed on either side of said Achilles tendon protrusion for attaching and protrusion to said layer of elastic material.

16. The shoe-foot interface of claim 15 wherein said cushioned layer further comprises a second cushioned layer having a higher shock absorbing capability disposed on the sole of the foot and covering the calcaneal prominence and the heads of the five metatarsal bones and extending along the arch of the foot.

17. The shoe-foot interface of claim 15 wherein said elastic layer extends up to and below the ankle.

18. The shoe-foot interface of claim 15 wherein said elastic layer extends up to and over the ankle bone on both the medial and lateral sides thereof.

* * * * *

UNITED STATES PATENT AND TRADEMARK OFFICE
CERTIFICATE OF CORRECTION

PATENT NO. : 4,476,858
DATED : October 16, 1984
INVENTOR(S) : R. Stephen Curtis

It is certified that error appears in the above-identified patent and that said Letters Patent is hereby corrected as shown below:

Col. 5, line 52, "of exerting" should be --or exerting--.

Col. 8, line 25, following "thereto," delete "and";

line 36, following "ankle" delete "." and insert --;--.

Signed and Sealed this

Sixteenth Day of April 1985

[SEAL]

Attest:

DONALD J. QUIGG

Attesting Officer     Acting Commissioner of Patents and Trademarks